United States Patent [19]

Hsu et al.

[11] Patent Number: 5,171,779
[45] Date of Patent: Dec. 15, 1992

[54] USE OF PLASMA TO IMMOBILIZE PROTEIN ON POLYMERIC SURFACES

[75] Inventors: Tien-Tsai Hsu; Mann-Tchao Wang, both of Taipei; Kuang-Pin Hsiung, Hsin-chu; Ging H. Hsiue, Hsinchu; Min-Shyan Sheu, Taipei, all of Taiwan

[73] Assignee: Industrial Technology Research Institute, Hsinchu, Taiwan

[21] Appl. No.: 687,224

[22] Filed: Apr. 18, 1991

Related U.S. Application Data

[62] Division of Ser. No. 220,570, Jul. 18, 1988, Pat. No. 5,028,657.

[51] Int. Cl.$^5$ ............... G01N 33/544; G01N 33/545; C12N 11/08; C12N 9/96
[52] U.S. Cl. .................................. 525/54.1; 435/180; 435/188; 530/402; 530/815; 436/528; 436/529; 436/530; 436/531
[58] Field of Search ............... 525/54.1; 435/180, 181, 435/182, 188; 530/402, 815; 436/523, 528, 529, 530, 531

[56] References Cited

U.S. PATENT DOCUMENTS

| | | | |
|---|---|---|---|
| 3,758,396 | 9/1973 | Vieth et al. | 435/179 |
| 3,839,175 | 10/1974 | Keyes | 435/176 |
| 4,039,413 | 8/1977 | Kraemer et al. | 525/54.1 |
| 4,240,889 | 12/1980 | Yoda et al. | 435/180 |
| 4,307,195 | 12/1981 | Karasawa et al. | 435/288 |

FOREIGN PATENT DOCUMENTS

0141627 5/1985 European Pat. Off. .

OTHER PUBLICATIONS

Hsiue et al., "Immobilization of Antibody on Porous Membrane for Insulin Enzyme Immunosensor", (Proc. Natl. Sci. Counc. ROC(A)), vol. 11, No. 6, 1987, pp. 483–487.

*Primary Examiner*—Nathan M. Nutter
*Attorney, Agent, or Firm*—Darby & Darby

[57] ABSTRACT

The present invention relates to a method of immobilizing proteins on a polymeric matrix by means of plasma activation and an apparatus and process for the use of such material. The protein mixture is applied to the surface of the polymeric matrix with or without the addition of a crosslinking agent. It is then placed into a plasma generator, wherein the functional groups on both the protein and the matrix molecules are activated to form free radicals. Upon returning from their high energy state, the free radicals form covalent bonds between the proteins and between the protein and the polymeric matrix. Using this method, the proteins are nonspecifically immobilized on the surface of the polymeric matrix. The method can be utilized to immobilize proteins on the surfaces of polymeric membranes, polymeric beads, polymeric tubes and polymeric plates. The immobilized protein has high biological activity and stability.

11 Claims, 12 Drawing Sheets

Fig. 18. [Sucrose] (mg/ml)

Fig. 19. [Sucrose] (mg/ml)

5,171,779

USE OF PLASMA TO IMMOBILIZE PROTEIN ON POLYMERIC SURFACES

This is a division of application Ser. No. 07/220,570, filed Jul. 18, 1988, and now U.S. Pat. No. 5,028,657.

BACKGROUND OF THE INVENTION

The subject invention relates to the use of a plasma activation method to induce protein immobilization on a polymeric matrix. There are many protein immobilization methods which are available to immobilize protein on different kinds of materials, for example, chemical activation, entrapment and crosslinking. These conventional methods suffer from many shortcomings such as forming products of low stability and low activity and the inability of any one method to work well with a variety of proteins.

In the processes of the prior art, plasma is used to immobilize proteins on a membrane surface only to induce polymerization of different monomers to entrap the protein molecules therein. This has been disclosed, in Japanese Patents Nos. 57-197034, 59-203951, 59-28476, 59-216587 and 61-87699.

SUMMARY OF THE INVENTION

The instant invention relates to a plasma activation method which can be used to immobilize a wide range of proteins on the polymeric matrix by using substantially one and the same technique.

More specifically, a protein mixture is first prepared with or without a crosslinking agent and then applied to a membrane. The treated membrane is placed into the reaction chamber which acts as a plasma generator and a vacuum drier. The plasma is generated in a nitrogen, oxygen or ammonia environment under the desired conditions of pressure and temperature, for a defined period of time, to properly activate the protein and membrane molecules without damaging the normal configuration of the protein molecules. The covalent bonds formed among protein molecules and protein-membrane molecules anchor the protein to the surface of the membrane and stabilize the protein configuration. After the reaction is completed, the membrane is removed from the reaction chamber and washed with a buffer solution to remove the unbound protein. The treated membranes may be stored in the buffer solution for later use or used directly.

By using the method of the invention, a protein membrane having good activity and stability can be produced. It may be used for many biotechnological and biomedical applications, for example, as a membrane reactor in biotransformation process, as an enzyme membrane in biosensing instruments, and as an antigen-antibody membrane in immunoassays.

The novel plasma activation method can be used to immobilize the protein on the polymeric matrix regardless of the form of the latter's surfaces. Accordingly, the present invention may be used to form myriad biosensors and many types of protein matrices in large or small quantities, including the large scale production of protein membranes. The use of the process for immobilizing glucose oxidase, lactate oxidase, 1-glutamate decarboxylase, 1-lysine decarboxylase and invertase, mutarotase, and glucose oxidase mixtures for the biosensing instrument purpose has already been established.

DETAILED DESCRIPTION OF THE INVENTION

A wide variety of proteins may be immobilized in accordance with the instant invention. In addition to those set forth above, these include, for example, glucose oxidase, 1-glutamate decarboxylase, 1-lysine decarboxylase, urease, uricase, insulin monoclonal antibody, phenol oxidase, alkaline phosphatase, invertase and mutarotase.

Polymeric materials which may be used to immobilize the proteins include polyolefins such as hydrophobic and hydrophilic polyethylene and polypropylene and cellulose acetate, e.g., cuprophane film. Hydrophilic polypropylene membranes are most preferred. It will be understood, however, that many plastics, elastomers, and fibers having similarly reactive surfaces may be treated with the protein under appropriate reaction conditions.

The particular surface configuration of the polymeric material may vary widely, depending on the desired application. Most preferably a membrane type surface is employed, though beads, plates and tubes may conveniently be used.

In the plasma generator, a variety of gases may be used to form the plasma. These include nitrogen, oxygen, and ammonia. A typical plasma generator is the radio frequency (13.56 MHz) generator PE-II Plasma System made by Technics Co.

The temperature during the plasma generation may range from 0° to 40° C., preferably from 0° to 25° C. The pressure may range from 0.1 to 0.4 torr, preferably from 0.1 to 0.2 torr. The power applied to the plasma generator will generally range from 25 to 300 watts, preferably from 50 to 300 watts. The time necessary for activation ranges from 1 to 10 minutes, preferably from 3 to 5 minutes.

As noted above, the plasma activation may take place in the presence of crosslinking agents such as glutaraldehyde. The preferred agent and optimum amount used may be readily determined by those skilled in the art.

After the activation, the treated product is rinsed in a buffer solution to remove unbound protein. A variety of buffer solutions may be employed for this washing step, as well as for storage. Examples of buffers include phosphate buffers, tris buffers and citric buffers. The concentration used may be readily determined and is dependent on the protein employed.

The immobilized protein may be used in biotransformation or biosensing instruments, as well as for immunoassays. For instance, immobilized tyrosinase may be used in the bioconversion of tyrosine to 1-DOPA and insulin monoclonal antibody can be used to assay the insulin content in clinical samples. Other than these examples, other applications of immobilized protein are well known in biotechnology and protein engineering.

As a general matter, in carrying out the invention, a protein solution is first prepared by dissolving the protein in the buffer with or without a crosslinking reagent. The polymeric material is cut into appropriate shapes and dimensions, washed with distilled water or NaOH solution to remove any contamination, and dried. The protein solution is pipetted onto the pretreated membrane and spread evenly with a spatula to form the samples.

Figure 1:
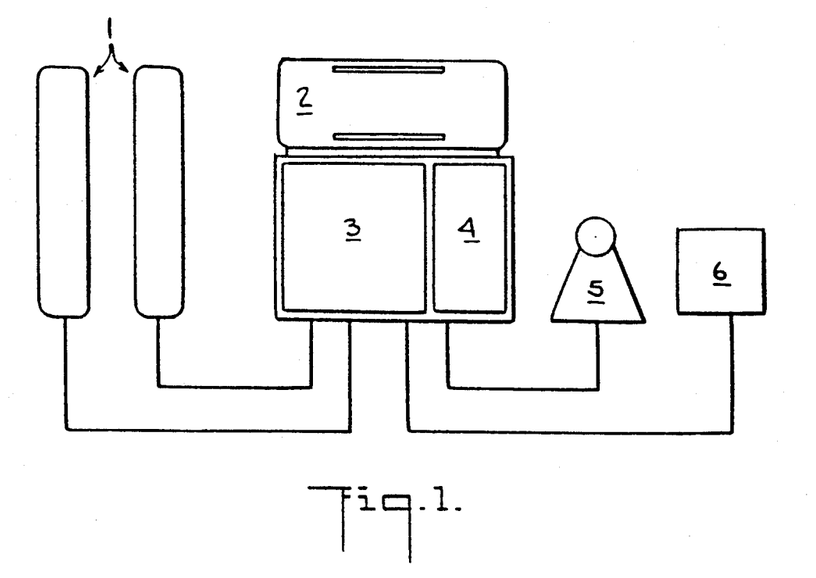
FIG. 1 is a diagram showing the plasma deposition system.

The plasma apparatus (Technics Co.), shown in FIG. 1, is operated by sequentially turning on the gases (1), the main power (3), the vacuum pump (5) and the water circulation pump (6). The control switch is turned to manual (3) and the plasma power turned on. When the vacuum reaches 0.1 torr, plasma forms. The time is set when the plasma is ready for use.

The samples are loaded on the lower electrode by setting the control switch to auto (3) and turning on the vent switch to open the reaction chamber (2). The reaction chamber is then closed and the process initiated by pushing the start button (4). The process is then carried out in accordance with the preset conditions. After the process is completed, the reaction chamber is vented and the treated membrane samples removed. The treated protein membrane is washed several times with an appropriate buffer for at least 12 hours. The membrane prepared is then stored in a storage solution or used directly.

The protein membrane may be analyzed by using a FTIR spectrophotometer, by protein stain or any known protein determination methods. If the protein is an enzyme, then it can be analyzed by detection of the enzyme activity. If the protein is an antibody, then it can be measured by Enzyme Immuno Assay (EIA) or Radio Immuno Assay (RIA).

Figure 2:
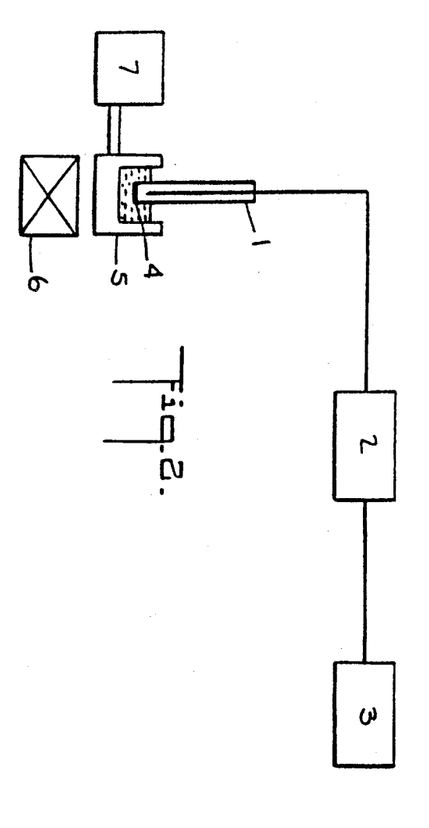
FIG. 2 shows the components of the biosensor.

In the present invention, the term "biosensor" means a device for determining the amount of a given substance. As shown in FIG. 2, it consists of transducer (1), analyzer (2), recorder (3), enzyme membrane (4), reaction chamber (5), stirrer (6) and temperature controller (7). When the biosensor employs an enzyme as the receptor it is also called an "enzyme sensor" and, if the enzyme sensor employs an electrochemical device as the transducer portion, then it is called an "enzyme electrode".

The following examples illustrate specific embodiments of the invention.

EXAMPLE 1: GLUCOSE ENZYME ELECTRODE

A hydrophilic polypropylene membrane is formed into a ring having an 8 mm inside diameter ("ID"). The shaped membrane is washed with 0.1M sodium chloride and distilled water, dried and stored in a dessicator for later use.

Twenty mg of glucose oxidase (EC 1.1.3.4) Type X (Sigma Co., U.S.A.) is dissolved in 1 ml of 0.1M potassium phosphate buffer at pH 5.5. Twenty mg of bovine serum albumin are dissolved in 1 ml of the same buffer. To complete enzyme solution preparation, the two solutions are mixed together.

On each membrane 5 microliter of enzyme solution is applied to form the sample. The sample is placed in a nitrogen plasma reaction chamber set to 0.1 torr, 125 watts, 4 minutes and 10° C. After treatment, the enzyme membrane is washed several times with 0.1M potassium phosphate buffer at pH 5.5 for 12 hours to remove the unbound proteins.

A kit containing the following components is then prepared as described below:

A) Buffer solution: Dissolve $K_2HPO_4$ and $KH_2PO_4$ in distilled water to make 0.1M potassium phosphate buffer, pH 5.5.

B) Glucose standard: Dissolve 0.64 g glucose in 100 ml distilled water then serially dilute to make 640, 320, 160, 80 and 40 mg/dl glucose standard.

C) Serum sample: From the hospital clinical laboratory.

D) Fermentation broth sample: Withdrawn from fermenter and diluted with buffer in 1:1 ratio to equilibrate the pH difference caused by fermentation process.

To measure the glucose, the instrument shown in FIG. 2 is used. The transducer (1) is a Clark's oxygen electrode and the analyzer (2) is an oxygen meter. The recorder (3) is Linseis 6512 strip chart recorder. The temperature is set to 30° C. (7).

The glucose oxidase membrane is held on the electrode surface with a cuprophane membrane and an O-ring. One-half ml of 1.6 g/dl glucose is added to adjust the zero oxygen tension. The chamber (5) is washed and refilled with 4.9 ml buffer to adjust span. When equilibrium is achieved, 0.1 ml of standard is used to develop the calibration curve. The sample is added and the concentration determined from the calibration curve.

Figure 3:
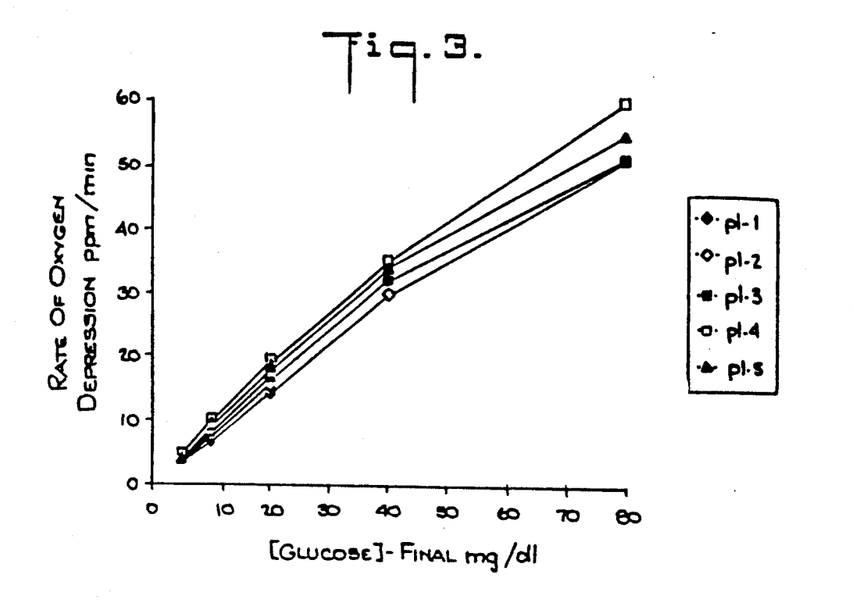
FIG. 3 is a graph showing the stability of a plasma activated glucose oxidase.
Figure 4A:
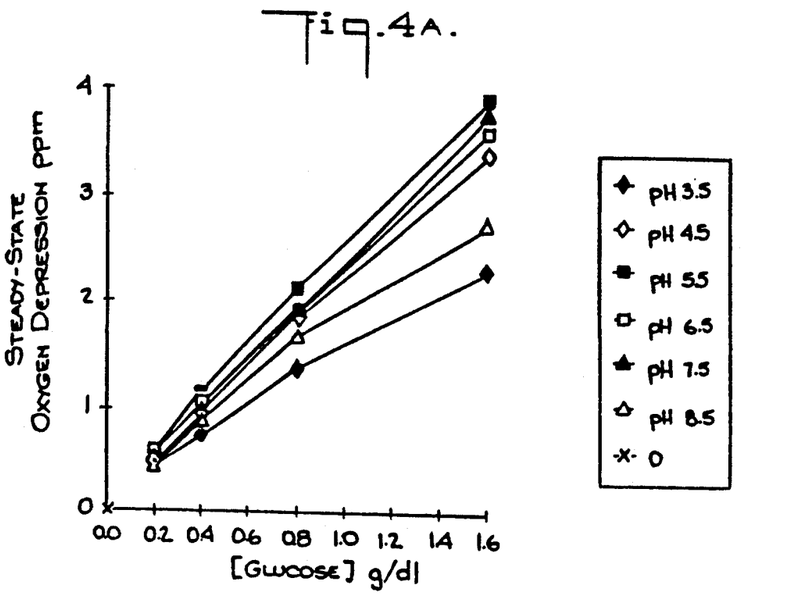
FIGS. 4A and 4B include two graphs showing that the optimum pH of a plasma treated glucose oxidase membrane ranges from 4.5 to 7.5. The upper graph shows the steady-state oxygen depression versus the glucose concentration at varied pH. The lower graph shows the slope of the curves set forth int he upper graph with respect to the pH.
Figure 4B:
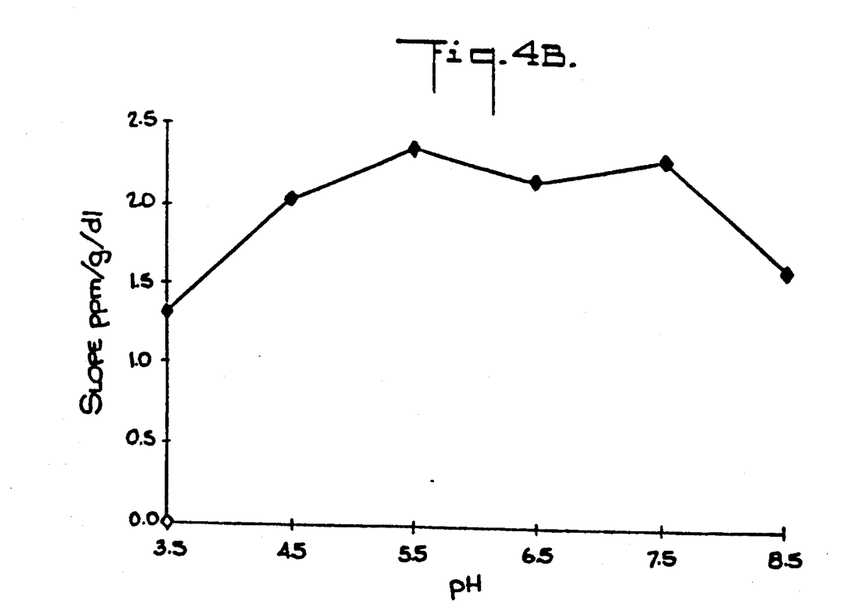
Figure 5A:
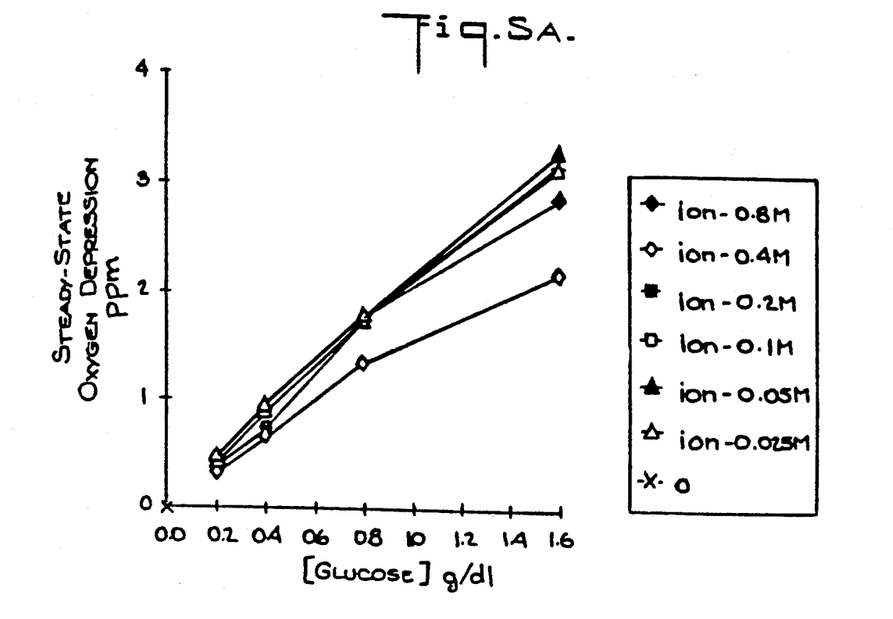
FIG. 5A and 5B include two graphs showing that the optimum buffer concentration of a plasma treated glucose oxidase membrane ranges from 0.1 to 0.8M in a Na-PB buffer. The upper graph shows the steady-state oxygen depression versus the glucose concentration at varied pH. The lower graph shows the slope of the curves set forth int he upper graph with respect to the pH.
Figure 5B:
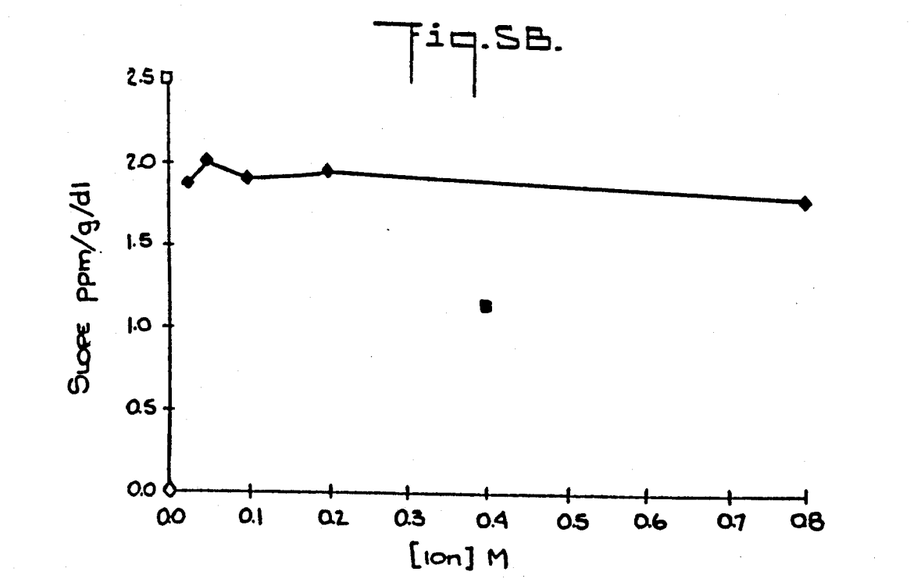
Figure 6:
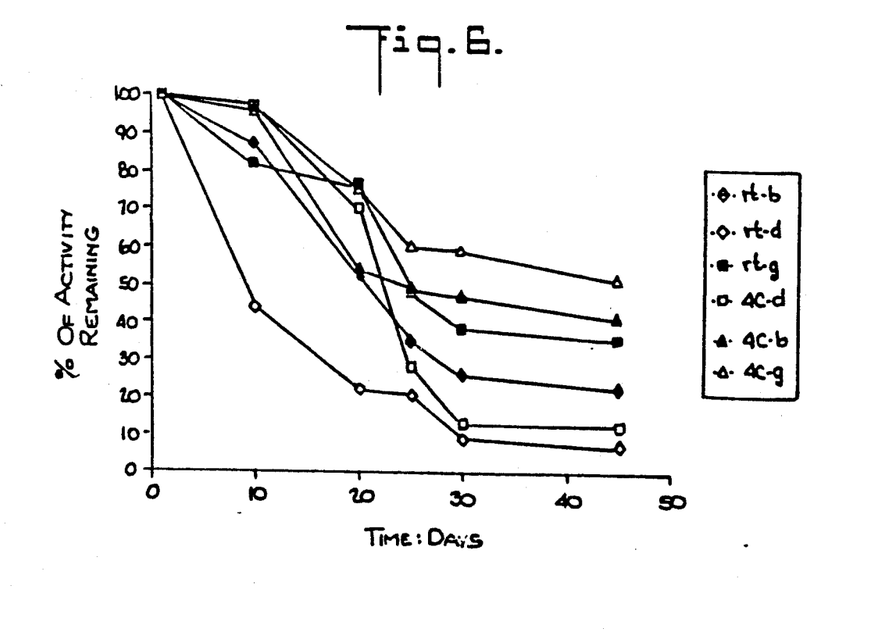
FIG. 6 is a graph showing the storage stability of a glucose oxidase membrane in a glycerol buffer.

From FIG. 3, it can be seen that the difference between different enzyme membrane prepared with plasma treatment is very small. The optimum pH range is from pH 4.5 to 7.5 (FIG. 4). The buffer concentration, ranging from 0.1M to 0.8M, has no influence on the glucose oxidase membrane (FIG. 5). The membrane, stored in glycerol buffer at 4° C. for 45 days, retains 50% of its original activity as shown in FIG. 6 and the following table:

TABLE

| Time (Days) | 1 | 10 | 20 | 25 | 30 | 45 |
|---|---|---|---|---|---|---|
| rt-dry | 100 | 44 | 22 | 20 | 8.9 | 6.7 |
| rt-buffer | 100 | 87 | 52 | 35 | 26 | 22 |
| rt-glycerol | 100 | 82 | 75 | 48 | 38 | 35 |
| 4° C.-dry | 100 | 97 | 70 | 28 | 13 | 12 |
| 4° C.-buffer | 100 | 96 | 54 | 49 | 47 | 41 |
| 4° C.-glycerol | 100 | 97 | 75 | 60 | 59 | 51 |

Figure 7:
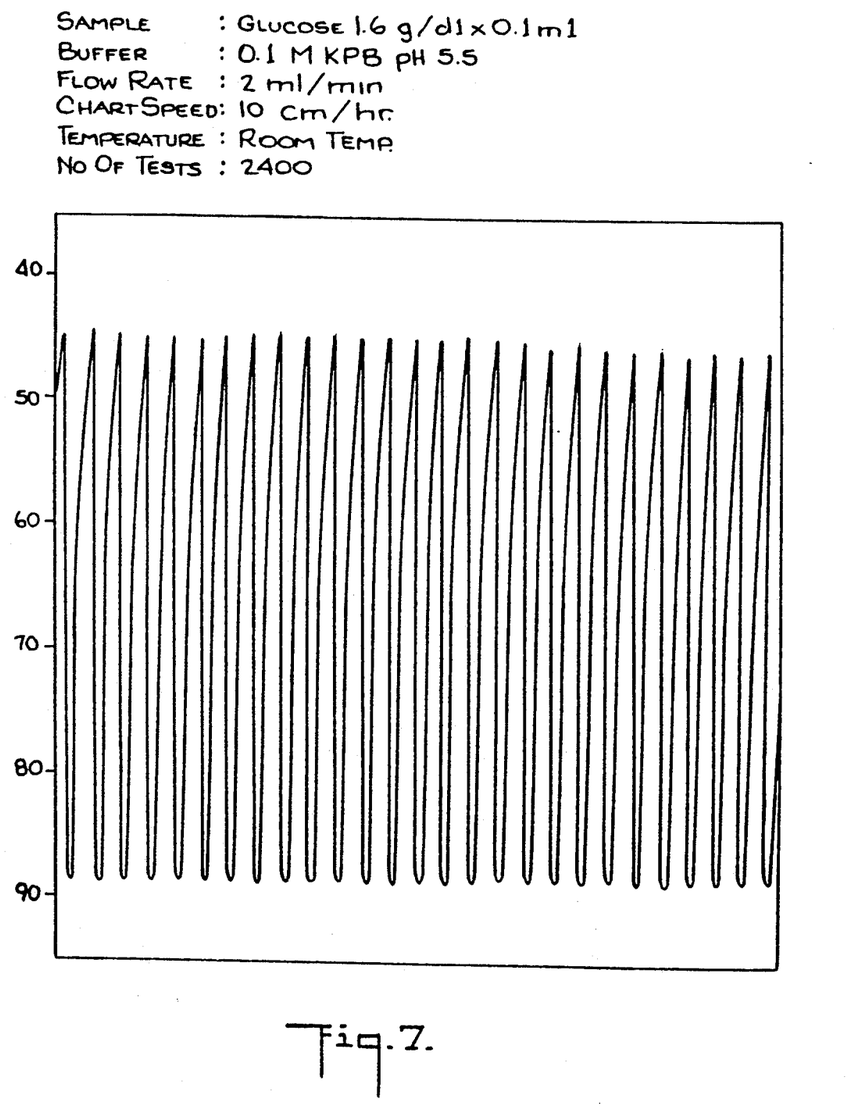
FIG. 7 is a graph showing the result of the analysis of the glucose standard.
Figure 8:
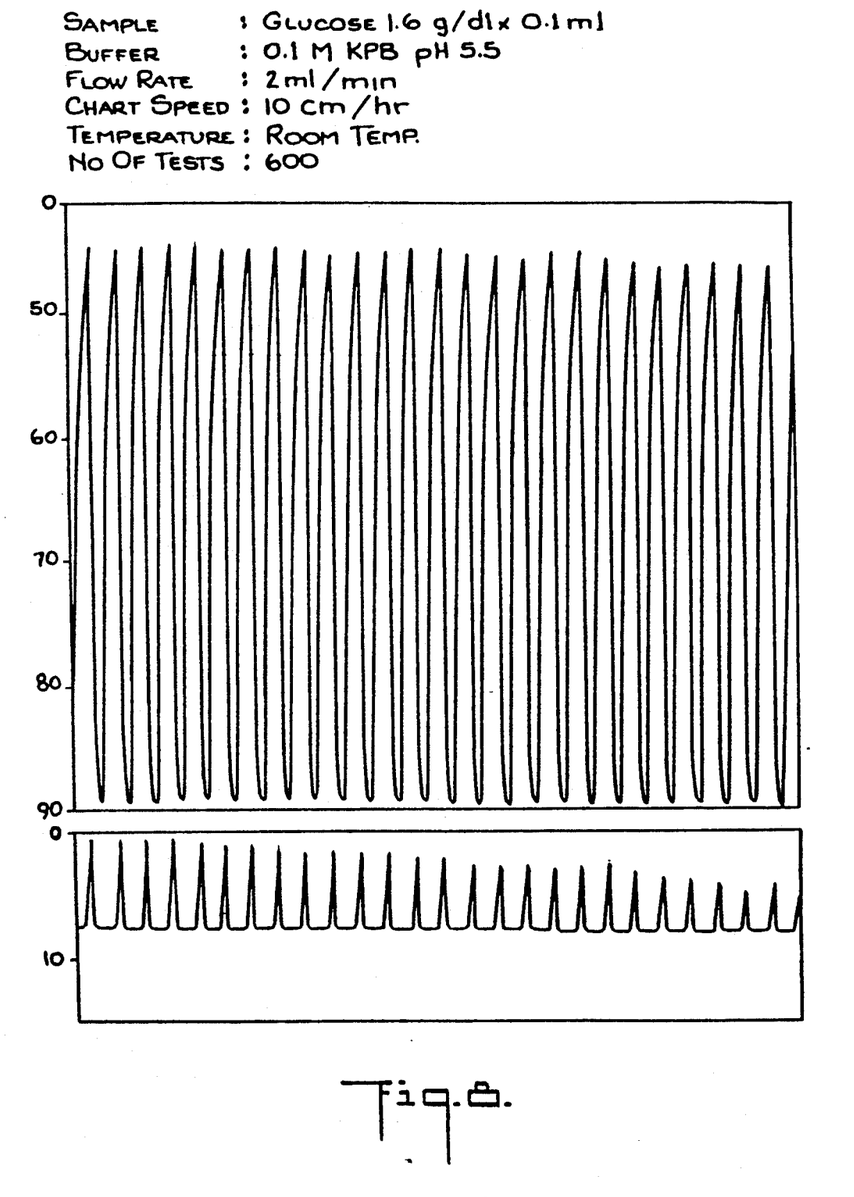
FIG. 8 is a graph showing the result of the analysis of a fermentation broth sample.

The membrane can perform 2400 glucose standard tests (FIG. 7) and 300 tests of the fermentation broth samples (FIG. 8).

The glucose oxidase membrane prepared as described above can be used not only as an enzyme electrode in the fermentation industry, but also for clinical tests for diabetes and in food processing for sweetness tests. It can also be used for the bioconversion of glucose into glutonic acid.

EXAMPLE 2: LACTIC ACID ENZYME ELECTRODE

A hydrophilic polypropylene membrane is cut into a 5 mm ID ring. The shaped membrane is washed with 0.1M sodium chloride and distilled water, dried and stored in a dessicator for later use.

Eight mg of glucose oxidase (lactate oxidase from Pediococcus species) (Sigma Co., U.S.A.) is dissolved in 1 ml of 0.1M potassium phosphate buffer at pH 7.0. Forty mg of bovine serum albumin are dissolved in 1 ml of the same buffer. To complete enzyme solution preparation, the two solutions are mixed together.

On each membrane 1 microliter of enzyme solution is applied to form the sample. The sample is placed in a nitrogen plasma reaction chamber set to 0.1 torr, 125 watts, 4 minutes and 10° C. After treatment, the enzyme membrane is washed several times with 0.1M potassium phosphate buffer at pH 7.0 for 12 hours to remove the unbound proteins.

A kit containing the following components is then prepared as described below:

A) Buffer solution: Dissolve $K_2HPO_4$ and $KH_2PO_4$ in distilled water to make 0.1M potassium phosphate buffer, pH 7.0.

B) Lactic acid standard: Dissolve 0.25 gm glucose in 100 ml distilled water then serially dilute to make 250, 200, 150, 100 and 50 mg/dl lactic acid standard.

C) Serum sample: From the hospital clinical laboratory.

D) Fermentation broth sample: Withdrawn from fermenter and diluted with buffer in 1:1 ratio to equilibrate the pH difference caused by fermentation process.

To measure the lactic acid, the transducer is an Able's hydrogen peroxide electrode and the analyzer is a hydrogen peroxide meter. The recorder is Linseis 6512 strip chart recorder. The temperature is set to 30° C.

The lactate oxidase membrane is held on the electrode surface with a cuprophane membrane and an O-ring. One-tenth ml of 2.5 g/dl lactic acid is added to adjust the zero hydrogen peroxide tension. The chamber (5) is washed and refilled with 4.9 ml buffer to adjust span. When equilibrium is achieved, 0.1 ml of standard is used to develop the calibration curve. The sample is added and the concentration determined from the calibration curve.

Figure 9:
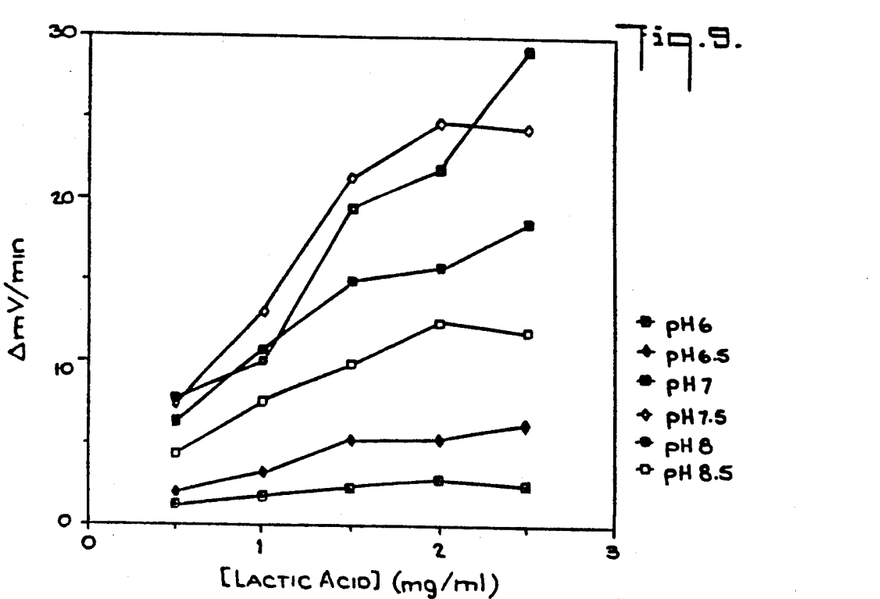
FIG. 9 is a graph showing that the optimum pH of a plasma treated lactate oxidase membrane ranges from 6.5 to 8.0.
Figure 10:
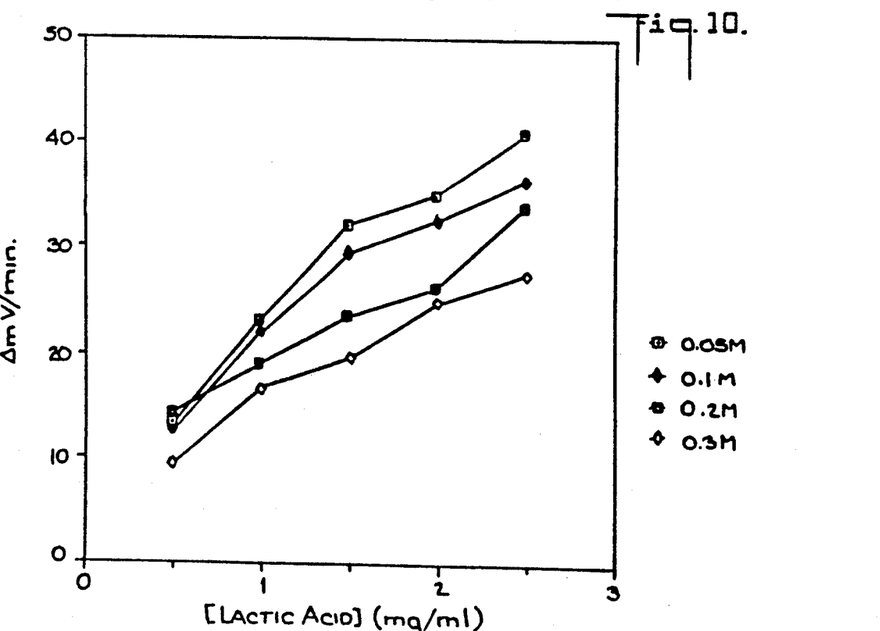
FIG. 10 is a graph showing that the optimum buffer concentration of a plasma treated lactate oxidase membrane ranges from 0.05 to 0.1M in a KPB buffer.
Figure 11:
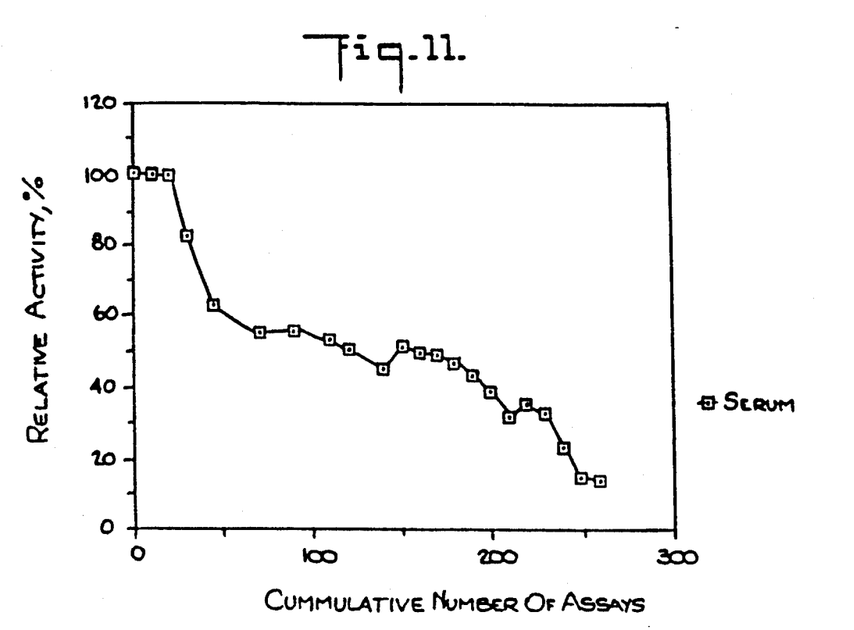
FIG. 11 is a graph showing the durability of lactate oxidase membrane.

It was determined that the optimum pH range is from 6.5 to 8.0 (FIG. 9) and that the buffer concentration range of from 0.05M to 0.1M had no influence on the lactate oxidase membrane (FIG. 10). The membrane can perform 200 tests on serum samples, while still retaining 30% of its original activity (FIG. 11). The membrane, stored in glycerol bufferate at 4° C., has activity for over four months.

The lactate oxidase membrane prepared in this manner can be applied not only to a lactic acid enzyme electrode for clinical, fermentation and food industries, but also for lactic acid production.

EXAMPLE 3: GLUTAMIC ACID ENZYME ELECTRODE

A hydrophilic polypropylene membrane is cut into an 11 mm ID ring. The shaped membrane is washed with 0.1M sodium chloride and distilled water, dried and stored in a dessicator for later use.

Twenty-nine mg of l-glutamate decarboxylase (EC 4.1.1.15) (Sigma Co., U.S.A.) is dissolved in 1 ml of 0.02M citric buffer at pH 4.5 and 60 mg of bovine serum albumin are dissolved in 1 ml of the same buffer. In addition, GA is dissolved in the same buffer to form 0.5 ml of a 1.56% solution. To complete enzyme solution preparation, the two solutions are mixed together.

On each membrane 5 microliter of enzyme solution is applied to form the sample. The sample is placed in a nitrogen plasma reaction chamber set to 0.1 torr, 125 watts, 4 minutes and 10° C. After treatment, the enzyme membrane is washed several times with 0.02M citric buffer at pH 4.5 for 12 hours to remove the unbound proteins.

A kit containing the following components is then prepared as described below:

A) Buffer solution: Dissolve 0.214 gm citric acid and 0.389 gm sodium citrate in 100 ml distilled water to make 100 ml 0.02M citric buffer, pH 4.5.

B) 1-Glutamate standard: Dissolve 0.32 gm 1-glutamate in 100 ml distilled water then serially dilute to make 1.6, 0.8, 0.4 and 0.2 gm/dl 1-glutamate standard.

C) Fermentation broth sample: Withdrawn from fermenter and diluted with buffer in 1:16 ratio to equilibrate the pH difference caused by fermentation process.

To measure the l-glutamate, the transducer is an ORION carbon dioxide electrode and the analyzer is an ORION pH meter. The recorder is Linseis 6512 strip chart recorder. The temperature is set to 30° C.

The l-glutamate decarboxylase membrane is held on the electrode surface with a cuprophane membrane and an O-ring. Four and one-half ml of buffer are added. When equilibrium is achieved, 0.5 ml of standard is used to develop the calibration curve. The sample is added and the concentration determined from the calibration curve.

Figure 12:
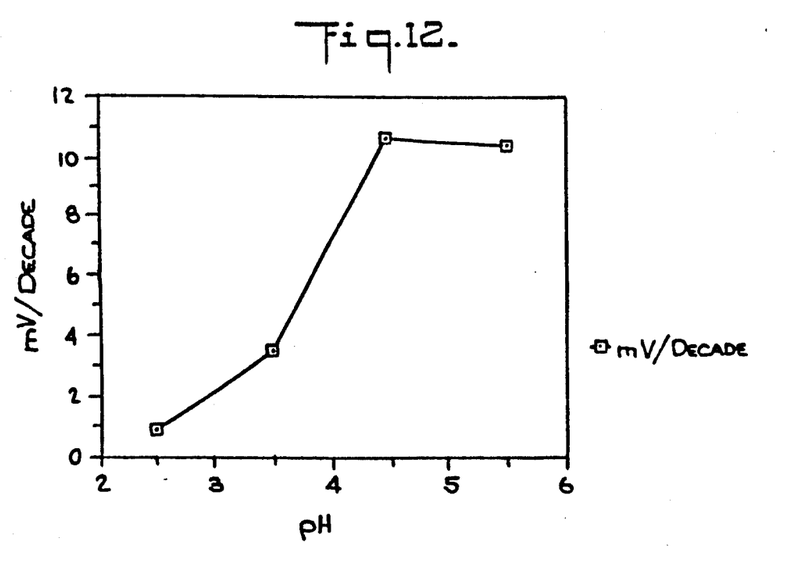
FIG. 12 is a graph showing that the optimum pH of a plasma treated 1-glutamate decarboxylase membrane ranges from 2.5 to 6.5.
Figure 13:
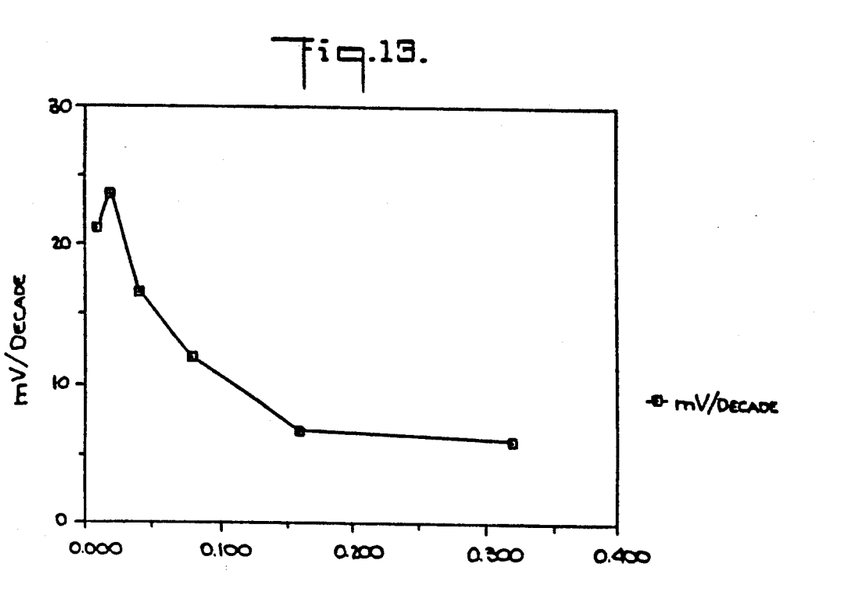
FIG. 13 is a graph showing that the optimum buffer concentration of a plasma treated 1-glutamate decarboxylase membrane ranges from 0.1 to 3.2M in a citric buffer.
Figure 14:
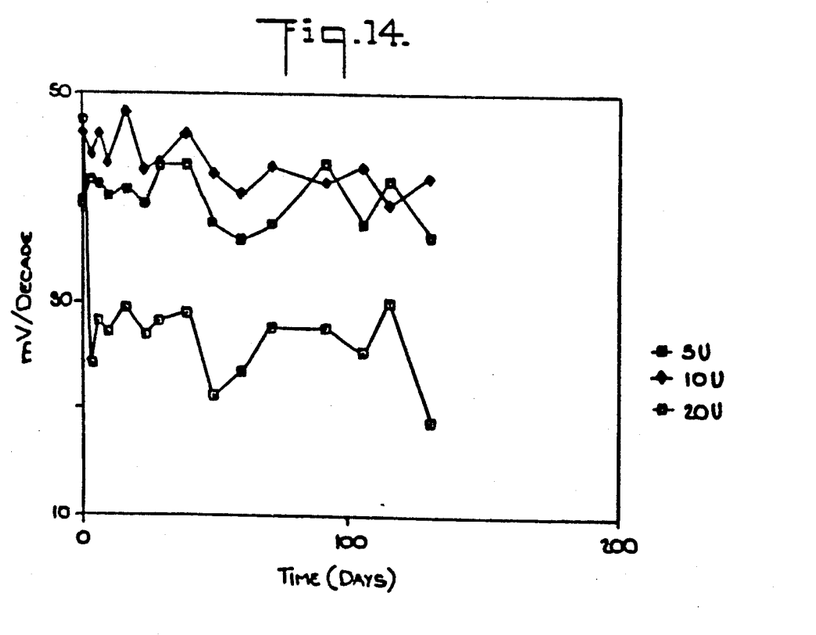
FIG. 14 is a graph showing the storage stability of 1-glutamate decarboxylase membrane at 4° C.
Figure 15A:
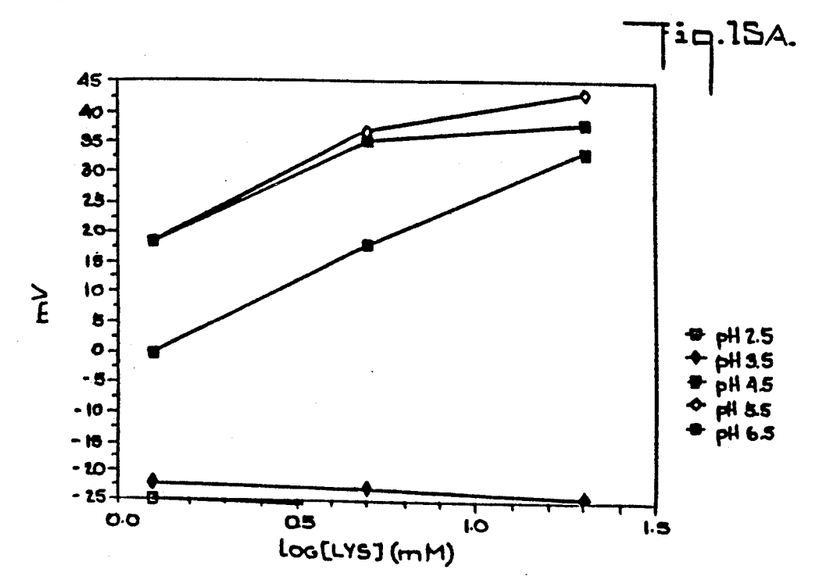
FIGS. 15A and 15B include two graphs showing that the optimum pH of a plasma treated 1-lysine decarboxylase membrane ranges from 2.5 to 6.5. The upper graph shows the calibration curve for the 1-lysine concentration. The lower graph shows the optimum pH for measuring the 1-lysine concentration.
Figure 15B:
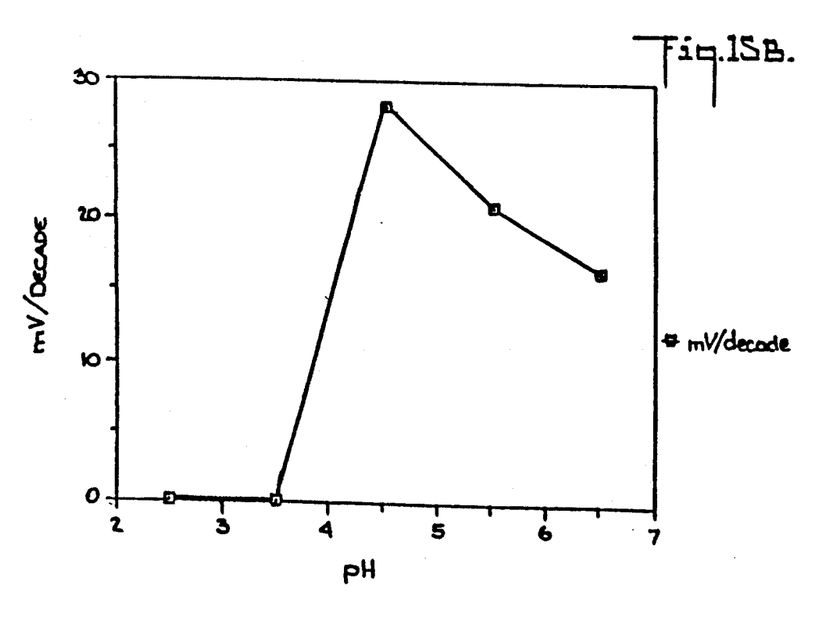

The data show the optimum pH is 4.5 (FIG. 12) and the optimum buffer concentration range 0.02M for the l-glutamate decarboxylase membrane (FIG. 13). The membrane, stored in glycerol buffer at 4° C. for 90 days, retained 50% of its original activity (FIG. 14).

The enzyme electrode prepared by the immobilized glutamate decarboxylase can be used to detect the glutamic acid content in food additives and in fermentation processes.

EXAMPLE 4: LYSINE ENZYME ELECTRODE

A hydrophilic polypropylene membrane is cut into an 11 mm ID ring. The shaped membrane is washed with 0.1M sodium chloride and distilled water, dried and stored in a dessicator for later use.

Twenty-nine and one-half mg of l-lysine decarboxylase (EC 4.1.1.18) Type VII (Sigma Co., U.S.A.) is dissolved in 1 ml of 0.01M citrate buffer at pH 4.5. Three and three-quarters mg of bovine serum albumin are dissolved in 1 ml of the same buffer. In addition, GA is dissolved in the same buffer to form 0.5 ml of a 1.56% solution. To complete enzyme solution preparation, the solutions are mixed together.

On each membrane 5 microliter of enzyme solution is applied to form the sample. The sample is placed in a nitrogen plasma reaction chamber set to 0.1 torr, 125 watts, 4 minutes and 10° C. After treatment, the enzyme membrane is washed several times with 0.01M citric buffer at pH 4.5 for 12 hours to remove the unbound proteins.

A kit containing the following components is then prepared as described below:

A) Buffer solution: Dissolve 0.11 gm citric acid and 0.20 gm sodium citrate in 100 ml distilled water to make 100 ml 0.01M citric buffer, pH 4.5.

B) l-Lysine standard: Dissolve 18.25 gm lysine in 100 ml distilled water then serially dilute to make 9.13, 4.56, 2.28 and 1.14 mg/dl l-lysine standard.

To measure the l-lysine, the instrument shown in FIG. 2 is used. The transducer is an ORION carbon dioxide electrode and the analyzer is an ORION pH meter. The recorder is Linseis 6512 strip chart recorder. The temperature is set to 30° C.

The l-lysine decarboxylase membrane is held on the electrode surface with a cuprophane membrane and an O-ring. Four and nine-tenths ml of buffer are added. When equilibrium is achieved, 0.1 ml of standard is used to develop the calibration curve. The sample is added and the concentration determined from the calibration curve.

Figure 16:
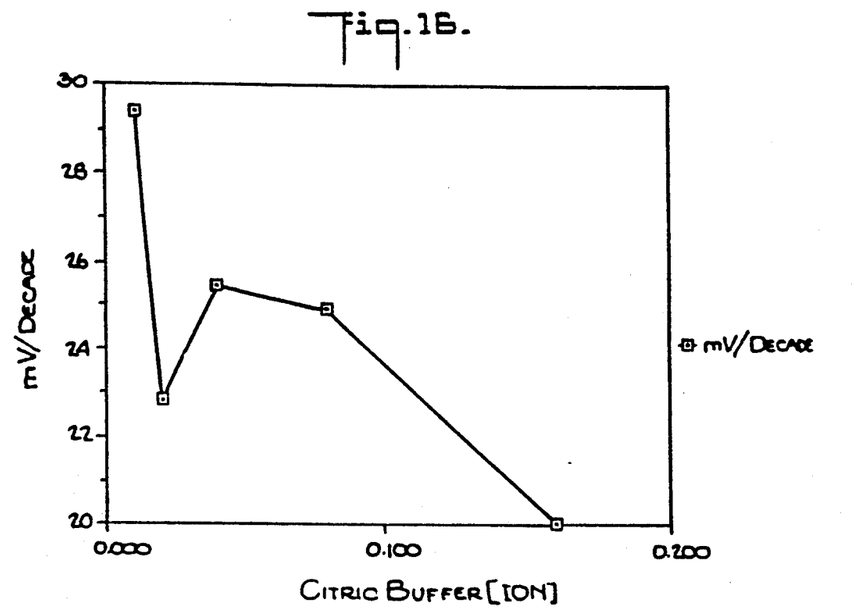
FIG. 16 is a graph showing that the optimum buffer concentration of the plasma treated 1-lysine decarboxylase membrane ranges from 0.1 to 3.2M in a citric buffer.
Figure 17:
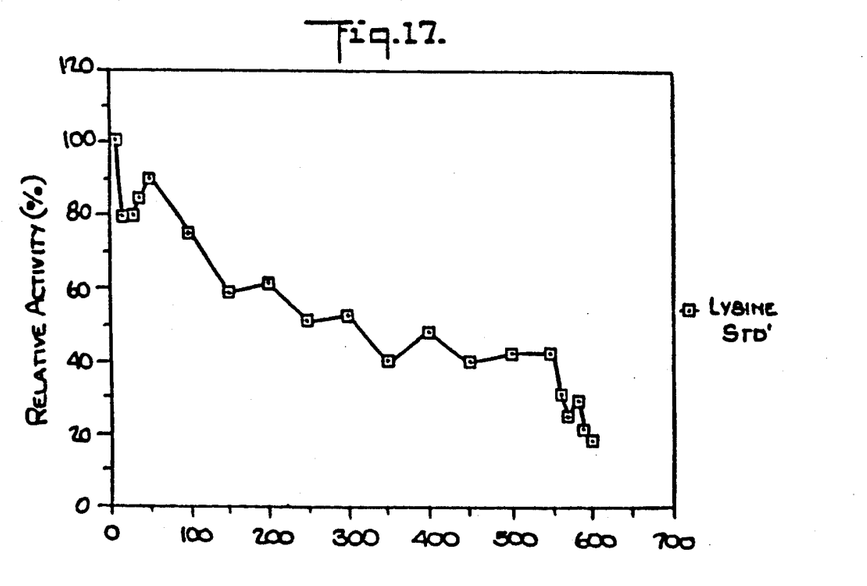
FIG. 17 is a graph showing the result of the analysis of the 1-lysine standard.

It can be seen that the optimum pH is 4.5 (FIG. 15) and the optimum buffer concentration range 0.01M (FIG. 16) for the l-lysine decarboxylase membrane. The analysis of the l-lysine standard is shown in FIG. 17.

The enzyme electrode prepared by the immobilized lysine decarboxylase can be used to detect the lysine content in food additives and in fermentation processes.

EXAMPLE 5: SUCROSE ENZYME ELECTRODE

A hydrophilic polypropylene membrane is cut into a 5 mm ID ring. The shaped membrane is washed with 0.1M sodium chloride and distilled water, dried and stored in a dessicator for later use.

Forty mg of glucose oxidase, 100 mg invertase, 10 mg mutarotase, 20 mg of bovine serum albumin are dissolved in 1 ml of 0.1M potassium phosphate buffer at pH 6.5.

On each membrane 2 microliter of enzyme solution is applied to form the sample. The sample is placed in a nitrogen plasma reaction chamber set to 0.1 torr, 125 watts, 4 minutes and 10° C. After treatment, the enzyme membrane is washed several times with 0.01M potassium phosphate buffer at pH 6.5 for 12 hours to remove the unbound proteins.

A kit containing the following components is then prepared as described below:

A) Buffer solution: Dissolve $K_2HPO_4$ and $KH_2PO_4$ in distilled water to make 0.1M potassium phosphate buffer, pH 6.5.

B) Sucrose standard: Dissolve 2 gm sucrose in 100 ml distilled water then serially dilute to make 2, 1.6, 1.2, 0.8 and 0.4 g/dl sucrose standard.

C) Serum sample: From the hospital clinical laboratory.

D) Fermentation broth sample: Withdrawn from fermenter and diluted with buffer in 1:1 ratio to equilibrate the pH difference caused by fermentation process.

To measure the sucrose, the transducer is an Able's hydrogen peroxide electrode and the analyzer is a hydrogen peroxide meter. The recorder is Linseis 6512 strip chart recorder. The temperature is set to 30° C.

The sucrose enzyme membrane is held on the electrode surface with a cuprophane membrane and an O-ring. One-tenth ml of 2 g/dl lactic acid is added to adjust the zero hydrogen peroxide tension. Four and nine-tenths ml of buffer are added. When equilibrium is achieved, 0.1 ml of standard is used to develop the calibration curve. The sample is added and the concentration determined from the calibration curve.

Figure 18:
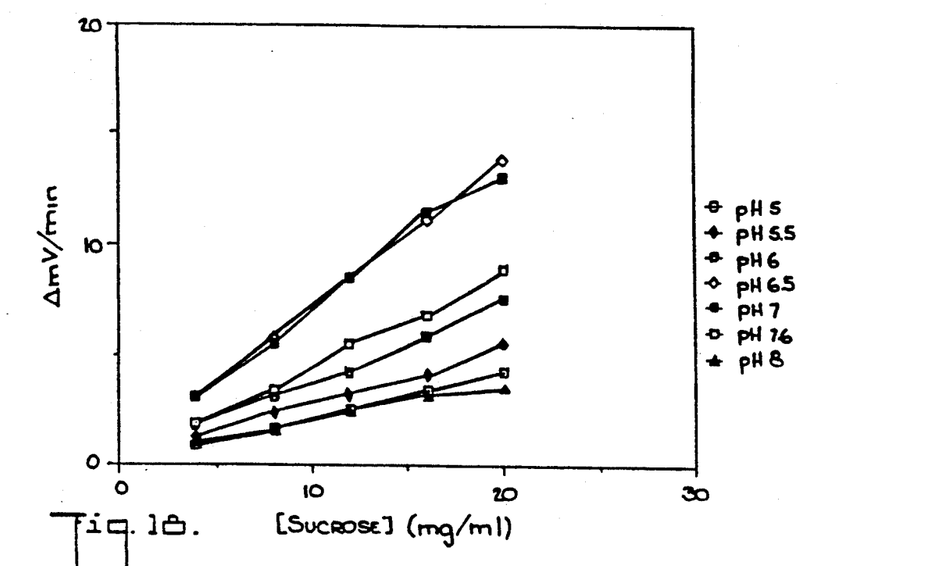
FIG. 18 is a graph showing that the optimum pH of a plasma treated sucrose enzyme membrane ranges from 6.5 to 7.0.
Figure 19:
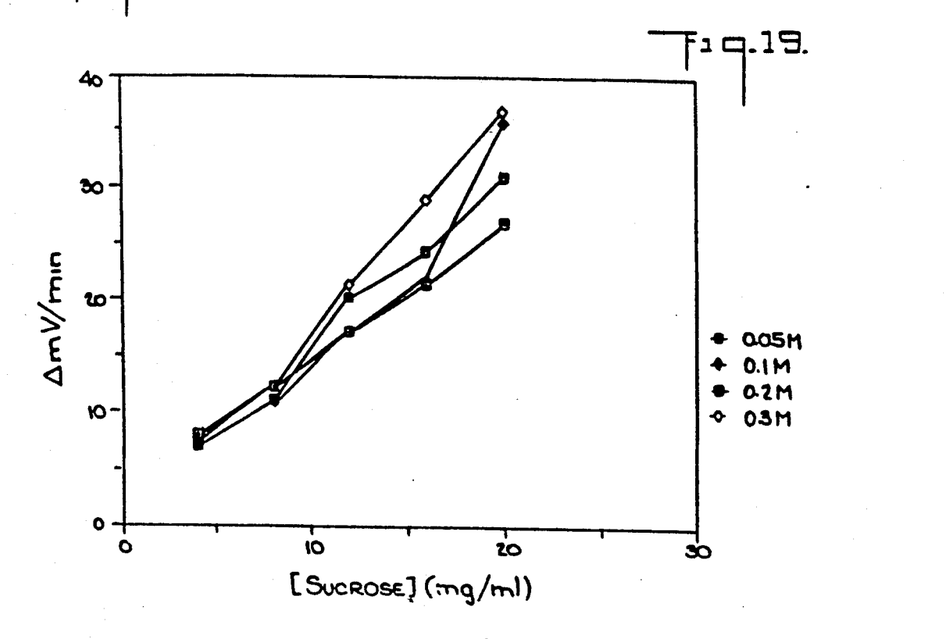
FIG. 19 is a graph showing that the optimum buffer concentration of a plasma treated sucrose enzyme membrane ranges from 0.1 to 0.3M in a KPB buffer.

The data show that the optimum pH range is from 6.5 to 7.0 (FIG. 18). The buffer concentration range from 0.1M to 0.3M has no influence on the sucrose enzyme membrane (FIG. 19). The membrane, stored in glycerol buffer at 4° C., has activity for over one month.

What is claimed is:

1. An article which comprises a protein immobilized to the surface of a polymer prepared by coating said polymer surface with a solution of said protein; exposing said coated polymer to an environment containing a gas plasma to form free radicals; and covalently bonding said protein to said polymeric surface at free radical sites.

2. The article of claim 1 wherein said exposure takes place in the presence of a crosslinking agent.

3. The article of claim 1 wherein said plasma is a nitrogen, an oxygen, or an ammonia plasma.

4. The article of claim 1 wherein the exposure temperature is from 0° to 25° C.

5. The article of claim 1 wherein the exposure pressure is from 0.1 to 0.2 torr.

6. The article of claim 1 wherein the power generated during said exposure is from 50 to 300 watts.

7. The article of claim 1 wherein the polymer is in the form of a membrane.

8. The article of claim 1 wherein the polymer is a bead.

9. The article of claim 1 wherein the polymer is a plate.

10. The article of claim 1 wherein the polymer is a tube.

11. The article of claim 1 wherein the protein is glucose oxidase, lactate oxidase, l-glutamate decarboxylase, l-lysine decarboxylase and invertase, mutarotase, or glucose oxidase mixtures.

* * * * *